(12) United States Patent
Rajagopalan

(10) Patent No.: US 7,655,828 B2
(45) Date of Patent: Feb. 2, 2010

(54) DISPOSABLE ABSORBENT ARTICLE HAVING A PATTERNED ODOR/ANTIMICROBIAL REDUCTION LAYER

(75) Inventor: Vijay Rajagopalan, Higashinada-ku (JP)

(73) Assignee: The Procter & Gamble Company, Cincinnati, OH (US)

( * ) Notice: Subject to any disclaimer, the term of this patent is extended or adjusted under 35 U.S.C. 154(b) by 1056 days.

(21) Appl. No.: 11/114,490

(22) Filed: Apr. 26, 2005

(65) Prior Publication Data

US 2005/0197641 A1 Sep. 8, 2005

Related U.S. Application Data

(63) Continuation of application No. 10/149,212, filed on Jun. 7, 2002, now abandoned.

(51) Int. Cl.
*A61F 13/15* (2006.01)
(52) U.S. Cl. .................................. 604/359; 604/360
(58) Field of Classification Search .............. 604/359, 604/360
See application file for complete search history.

(56) References Cited

U.S. PATENT DOCUMENTS 3,585,998 A    6/1971  Hayford
3,762,415 A   10/1973  Morrison
3,939,838 A    2/1976  Fujinami
4,547,195 A   10/1985  Jackson
5,047,022 A *  9/1991  Hasebe et al. ............... 604/359
5,342,333 A *  8/1994  Tanzer et al. ................ 604/359
5,733,273 A    3/1998  Ahr
5,792,855 A *  8/1998  Yonemura et al. ............. 536/56
5,830,543 A * 11/1998  Miyake et al. ............. 428/35.2

FOREIGN PATENT DOCUMENTS

EP       0 253 890 A1    1/1988
EP       0 386 723 A1    9/1990
EP       0 592 001 A1    4/1994
WO     WO 96/24318 A1    8/1996

* cited by examiner

*Primary Examiner*—Tatyana Zalukaeva
*Assistant Examiner*—Lynne Anderson
(74) *Attorney, Agent, or Firm*—Jason J. Camp; Gary J. Foose

(57) ABSTRACT

The present invention is directed to a disposable absorbent article. The disposable absorbent article of the present invention includes: a topsheet, a backsheet combined with the topsheet, a fluid storage layer disposed between the topsheet and backsheet and having a body-facing surface and a garment-facing surface opposing the body-facing surface. The disposable absorbent article further includes an odor/antimicrobial reduction layer disposed either between the topsheet and the fluid storage layer or between the backsheet and the fluid storage layer. The odor/antimicrobial reduction layer contains an odor/antimicrobial material. The odor/antimicrobial reduction layer has a predetermined pattern of the odor/antimicrobial material.

11 Claims, 1 Drawing Sheet

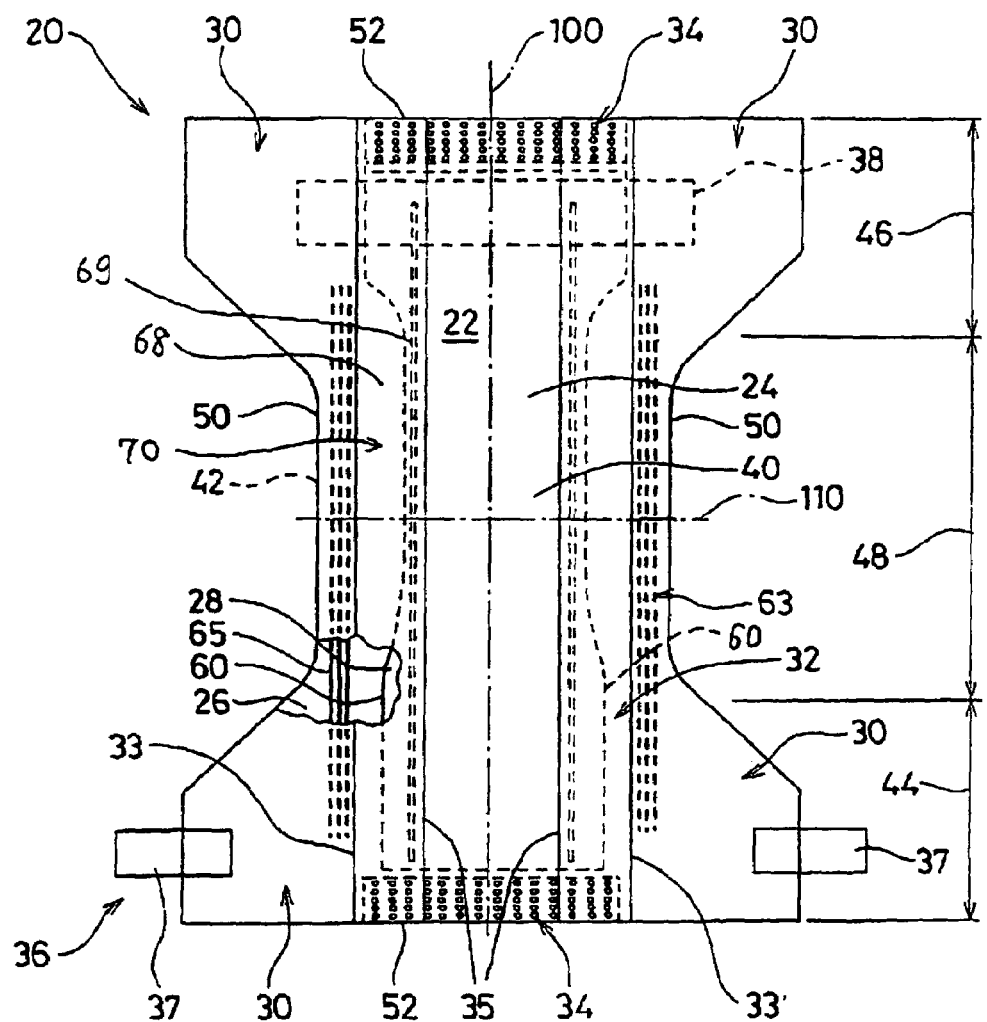
Figure

DISPOSABLE ABSORBENT ARTICLE HAVING A PATTERNED ODOR/ANTIMICROBIAL REDUCTION LAYER

CROSS REFERENCE TO RELATED APPLICATIONS

This application is a continuation of U.S. application Ser. No. 10/149,212, filed Jun. 7, 2002, pending.

FIELD

The present invention relates to disposable absorbent articles. More specifically, the present invention relates to disposable absorbent articles which employ an odor/antimicrobial reduction layer having a predetermined pattern of an odor/antimicrobial material. Examples of such disposable absorbent articles include disposable underwears, disposable diapers (adult and baby) including pull-on diapers and training pants, disposable panties for menstrual use, and disposable absorbent pads including sanitary napkins.

BACKGROUND

A wide variety of disposable absorbent articles are designed not only to be efficient in the absorption of body fluids such as urine, blood, menses and the like, but also to be sanitary and comfortable in-use, are known in literature. Disposable absorbent products of this type generally comprise a fluid-permeable topsheet material, an absorbent core (or a fluid storage layer), and a fluid-impermeable backsheet material. Various shapes, sizes and thicknesses of such articles have been explored in an attempt to make their use more comfortable and convenient.

For some time now, studies for such disposable absorbent articles have been primarily focused on the absorptive capacity of the article. As a result, various absorbent polymers with high absorptive power have been developed. Such known superabsorbent materials (also known as hydrogel-forming absorbent polymers) are capable of absorbing from about 30 to 60 grams of water per gram of polymer.

More recently, research has been focused on the removal of foul odors and the prevention of skin diseases such as dermatitis, rash and redness caused by wearing a disposable absorbent article for a relatively long time. Many body fluids have an unpleasant odor (or an malodor), or develop such an odor when in contact with air and/or bacteria for prolonged periods. Additionally, urine and/or other exudates absorbed into the absorbent article are converted to ammonia by urease produced by skin-flora, i.e., a group of normal microorganisms on the skin. This ammonia, in turn, may cause dermatitis, rash and/or other forms of skin irritation. Such disease of the skin in infants can be a serious medical matter which, in extreme cases, can result in death.

Antimicrobial materials and bactericides in general are chemical compositions that are used to prevent microbiological contamination and deterioration of products, materials, and systems. Such antimicrobial materials and bactericides can also effectively work for the removal or reduction of foul odors developed from disposable absorbent articles which has already absorbed body fluids. However, depending on the manner of the application of antimicrobial materials or bactericides in disposable absorbent articles, it is found that such antimicrobial materials and bactericides tend to affect the absorptive capacity of disposable absorbent articles.

For example, Japanese Patent (Kokoku) Publication No. H4-17058 discloses a disposable diaper which includes an absorbent layer containing a superabsorbent material and a antimicrobial material included in the superabsorbent material. Similarly, Japanese Patent (Kokai) Publication No. 145-277143 discloses a disposable diaper which includes a superabsorbent material containing an odor reduction material. Metalphthalocyanine derivatives are disclosed in H5-277143 as examples of the odor reduction material. Further, Japanese Patent (Kokai) Publication No. S64-25856 discloses a sanitary napkin which includes an absorbent sheet including a superabsorbent material and a metalphthalocyanine derivative as an odor reduction material. In those structures disclosed, the antimicrobial or odor reduction material is in contact with the superabsorbent material, as a result, the absorptive capacity of the superabsorbent material tends to be decreased because of the existence of the antimicrobial or odor reduction material.

To prevent the antimicrobial materials and/or bactericides from affecting the absorptive capacity of disposable absorbent articles, it is preferred that the antimicrobial materials and/or bactericides is provided in a layer which is isolated from the superabsorbent material. However, the antimicrobial materials and/or bactericides tend to be expensive and increase the manufacturing cost of the disposable absorbent articles, therefore, an appropriate (and a minimum) amount of the antimicrobial materials and/or bactericides needs to be used while providing an effective odor and/or antimicrobial reduction function. Further, it is not generally easy in the manufacturing process to control the total amount of the antimicrobial materials and/or bactericides which is applied to a component material(s) of disposable absorbent articles.

Based on the foregoing, there is a need for disposable absorbent articles which have an effective odor and/or antimicrobial reduction function with a minimum manufacturing cost increase. Further, there is also a need for disposable absorbent articles which have a structure that can easily control the total amount of odor and/or antimicrobial reduction material applied thereto.

SUMMARY

The present invention is directed to a disposable absorbent article. The disposable absorbent article of the present invention includes: a topsheet, a backsheet combined with the topsheet, a fluid storage layer disposed between the topsheet and backsheet and having a body-facing surface and a garment-facing surface opposing the body-facing surface. The disposable absorbent article further includes an odor/antimicrobial reduction layer disposed either between the topsheet and the fluid storage layer or between the backsheet and the fluid storage layer. The odor/antimicrobial reduction layer contains an odor/antimicrobial material. The odor/antimicrobial reduction layer has a predetermined pattern of the odor/antimicrobial material.

The foregoing answers the need for disposable absorbent articles which have an effective odor and/or antimicrobial reduction function with a minimum manufacturing cost increase. The foregoing also answers the need for disposable absorbent articles which have a structure that can easily control the total amount of odor and/or antimicrobial reduction material applied thereto.

These and other features, aspects, and advantages of the present invention will become evident to those skilled in the art from reading of the present disclosure.

BRIEF DESCRIPTION OF THE DRAWING

While the specification concludes with claims particularly pointing out and distinctly claiming the invention, it is believed that the invention will be better understood from the following description of preferred embodiments which is taken in conjunction with the accompanying a drawing and which like designations are used to designate substantially identical elements, and in which:

FIGURE is a simplified plan view of one preferred embodiment of the disposable absorbent article of the present invention in its flat uncontracted condition showing the body-facing side of the garment.

DETAILED DESCRIPTION

All cited references are incorporated herein by reference in their entireties. Citation of any reference is not an admission regarding any determination as to its availability as prior art to the claimed invention.

Herein, "comprise" and "include" mean that other element (s) and step(s) which do not affect the end result can be added. These terms encompass the terms "consisting of" and "consisting essentially of".

Herein, "nonwoven" may include any material which has been formed without the use of textile weaving processes which produce a structure of individual fibers which are interwoven in an identifiable manner. Methods of making suitable nonwovens includes a carded nonwoven process, a spunbonded nonwoven process, a meltblown nonwoven process, or the like.

Herein, "layer" does not necessarily limit the element to a single strata of material in that a layer may actually comprise laminates or combinations of sheets or webs of the requisite types of materials.

Herein, "joined" or "joining" encompasses configurations whereby an element is directly secured to another by affixing the element directly to the other element, and configurations whereby the element is indirectly secured to the other element by affixing the element to intermediate member(s) which in turn are affixed to the other element.

Herein, "metalphthalocyanine material" encompasses a metalphthalocyanine, its derivatives, and any mixture materials thereof.

Herein, "odor/antimicrobial reduction layer" encompasses a layer which includes a odor reduction material and/or an antimicrobial material (hereinafter referred to as "OAM") that can provide an odor reduction function and/or an antimicrobial reduction function in disposable absorbent articles.

The absorbent structures of the present invention can be utilized in disposable absorbent articles which are capable of absorbing significant quantities of body fluids, such as urine and water in body wastes. Examples of such disposable absorbent articles include disposable underwears, disposable diapers (adult and baby) including pull-on diapers and training pants, disposable panties for menstrual use, and disposable absorbent pads including sanitary napkins.

The disposable absorbent article of the present invention generally includes the following basic structural components: a topsheet, a backsheet combined with the topsheet, a fluid storage layer disposed between the topsheet and backsheet; and an odor/antimicrobial reduction layer disposed either between the topsheet and the fluid storage layer or between the backsheet and the fluid storage layer. Preferably, the fluid storage layer contains a superabsorbent material. The odor/antimicrobial reduction layer contains an odor/antimicrobial material. The odor/antimicrobial reduction layer has a predetermined pattern of the odor/antimicrobial material.

The odor/antimicrobial reduction layer is preferably disposed between the topsheet and the fluid storage layer. The odor/antimicrobial reduction layer may be disposed between the backsheet and the fluid storage layer. Preferably, the odor/antimicrobial reduction layer is disposed adjacent to either the body-facing surface or the garment-facing surface of the fluid storage layer such that it can be in contact with of the fluid storage layer. The topsheet can be either liquid pervious or liquid impervious. In a preferred embodiment, the topsheet is liquid pervious. Similarly, the backsheet can be either liquid pervious or liquid impervious. In a preferred embodiment, the backsheet is liquid impervious. The liquid pervious topsheet and backsheet can be formed by treating them with a finishing oil or a surfactant well known in the art. Further, the liquid impervious backsheet can be formed by employing an impervious thin plastic film. In a preferred embodiment, the disposable absorbent article further includes; a liquid pervious topsheet, and a liquid impervious backsheet combined with the topsheet.

The odor/antimicrobial reduction layer of the present invention has a predetermined pattern of the OAM which can provide an effective odor and/or antimicrobial reduction function in disposable absorbent articles. In a preferred embodiment, the odor/antimicrobial reduction layer includes a carrier means. The predetermined pattern is defined by a more-treated region and a less-treated region by the OAM. Herein, "more-treated region by the OAM" means a region of the odor/antimicrobial reduction layer having a weight to area ratio of the OAM greater than about 0.001 mg/cm$^2$, preferably greater than about 0.002 mg/cm$^2$, more preferably greater than about 0.005 mg/cm$^2$. Herein, "less-treated region by the OAM" means a region of the odor/antimicrobial reduction layer having a weight to area ratio of the OAM less than about 0.0005 mg/cm$^2$, preferably less than about 0.0003 mg/cm$^2$ more preferably less than about 0.0001 mg/cm$^2$. In a preferred embodiment, the less-treated region has a basis weight of the OAM of about 0 mg/cm$^2$, i.e., an untreated region by the OAM. Any predetermined pattern can be used, including, for example, application of small droplets, discrete dots, stripes that run in the longitudinal or lateral direction of the article, spirals that run in the longitudinal or lateral direction, pictures and/or characters, and the like.

In those embodiments, the percent less-treated area of the region of the odor/antimicrobial reduction layer can vary widely. Herein, "percent less-treated area" of the odor/antimicrobial reduction layer is determined by (i) measuring the total surface area of the odor/antimicrobial reduction layer (which includes the more-treated region(s) and the less-treated region(s) by the OAM), (ii) measuring the total surface area of the less-treated region(s) in the odor/antimicrobial reduction layer and (iii) dividing the measurement in (ii) by the measurement in (i). The percent less-treated area may be from about 1% to about 99%, preferably from about 5% to about 95%, more preferably from about 10% to about 90%, yet more preferably from about 15% to about 85%, still more preferably from about 20% to about 80%, yet more preferably from about 25% to about 75%, still more preferably from about 30% to about 70%, and yet more preferably from about 35% to about 65%.

The percent less-treated area required to achieve a desired odor and/or antimicrobial reduction function and the desired liquid handling properties of the odor/antimicrobial reduction layer will be dictated largely by the characteristics of the OAM (in particular the OAM's contents and its relative hydrophobicity/hydrophilicy properties). One skilled in the art will appreciate that the desired percent less-treated area will be readily determined through routine experimentation.

In a preferred embodiment, the OAM is applied to the odor/antimicrobial reduction layer in an average basis weight ranging from about 0.002 to 0.012 g/cm$^2$, more preferably from about 0.003 to 0.008 g/cm$^2$, still more preferably 0.004 to 0.007 g/cm$^2$. It will be recognized that for OAMs that are relatively hydrophilic, higher add-on levels may be used without adversely impacting liquid handling properties of the odor/antimicrobial reduction layer to an unacceptable degree. Of course, for articles having relatively high percent less-treated areas in the crotch, greater add-on levels may be obtainable without adversely affecting liquid handling by the odor/antimicrobial reduction layer.

In a preferred embodiment, the predetermined pattern of the odor/antimicrobial reduction layer is stripes (or spirals) of OAM that preferably run in the absorbent article's longitudinal direction. Preferably, each of these stripes has a width from about 0.1 cm to about 10 cm, more preferably, from about 0.5 cm to about 5 cm. These longitudinal stripes are spaced apart by the less-treated region(s) each of which has a width from about 0.1 cm to about 10 cm, more preferably from about 0.5 cm to about 5 cm where little or no OAM is applied to the odor/antimicrobial reduction layer. These ranges are applicable to typical adult incontinent products. For smaller products such as infant diaper designs, these ranges may be lower.

Many body fluids have an unpleasant odor (or an malodor), or develop such an odor when in contact with air and/or bacteria for prolonged periods. Additionally, urine and/or other exudates absorbed into the fluid storage layer are converted to ammonia by urease produced by skin-flora, i.e., a group of normal microorganisms on the skin. This ammonia, in turn, may cause dermatitis, rash and/or other forms of skin irritation. The principal function of the odor/antimicrobial reduction layer is to reduce such an unpleasant odor which is contained in and/or may be developed from the body fluid absorbed and retained in the fluid storage layer. The odor/antimicrobial material contained in the odor/antimicrobial reduction layer, upon contact with a body fluid, neutralizes the ammonia components contained in the absorbed body fluid through the neutralization.

Further, since the odor/antimicrobial reduction layer has a predetermined pattern of the odor/antimicrobial material in the disposable absorbent article of the present invention, an effective odor and/or antimicrobial reduction function can be achieved with a minimum manufacturing cost increase. Additionally, by using such a structure (i.e., the predetermined pattern of the odor/antimicrobial material) in disposable absorbent articles, the total amount of odor and/or antimicrobial reduction material applied thereto can be easily controlled in the manufacturing process for disposable absorbent articles.

The odor/antimicrobial reduction layer of the present invention can comprise a single layer of essentially 100% odor/antimicrobial material, or can also include a carrier means. Preferably, the odor/antimicrobial reduction layer contains at least from about 0.001% to about 10%, by weight, of the odor/antimicrobial material, and from about 90% to about 99.999% of the carrier means. More preferably, the odor/antimicrobial reduction layer contains at least from about 0.002% to about 0.2%, by weight, of the odor/antimicrobial material, and from about 99.998% to about 99.8% of the carrier means. In a preferred embodiment, the odor/antimicrobial reduction layer contains about 0.003% of the odor/antimicrobial material, and about 99.997% of the carrier means. The odor/antimicrobial material can be contained in the odor/antimicrobial reduction layer in any form which can be incorporated into the odor/antimicrobial reduction layer.

The carrier means holds or keeps the odor/antimicrobial material within the fluid storage layer through physical or chemical bonds. Any materials known in the art can be used as the carrier means as long as it can hold or keep the odor/antimicrobial material therein. Preferred carrier means includes fibrous materials such as nonwoven webs, tissue webs, and fluffs of synthetic fibers or natural fibers such as cellulose fibers; foams, apertured polymeric webs or films; and the like. Preferably, at least 95%, more preferably at least 99% by weight of the odor/antimicrobial material is physically bonded to the component material of the carrier means, while the rest of the odor/antimicrobial material may remain unbonded or chemically bonded to some of the component material of the carrier means.

In a preferred embodiment, the carrier means is a nonwoven material. More preferably, the nonwoven material is a resin bonded nonwoven material formed by polyethylene terephthalate (PET) fibers. A preferred resin bonded nonwoven material which can be used as the carrier means is commercially available from PGI Nonwovens, USA, under Code No. 68500.

In an alternative preferred embodiment, the carrier means is formed by a natural fibrous material such as cellulose fibers in the form of fluff, which is conventionally utilized and generally referred to as "airfelt" in absorbent cores (or fluid storage layers).

The odor/antimicrobial reduction layer may have a number of shapes and sizes. For example, the odor/antimicrobial reduction layer is typically in the form of rectangular, hourglass, or asymmetrical. The odor/antimicrobial reduction layer generally has a thickness or diameter between about 0.25 mm and about 10.0 mm. Preferably for use in absorbent products, the odor/antimicrobial reduction layer are in the form of rectangular having a thickness of greater than about 250 microns. The odor/antimicrobial reduction layer preferably has a thickness between about 0.5 mm and about 3 mm, typically about 1 mm.

The OAM useful in the present invention includes any chemical capable of controlling or reducing an unpleasant odor (or an malodor) contained in body fluids or developed when such body fluids are in contact with air and/or bacteria for prolonged periods. The OAM useful in the present invention also includes any chemical capable of preventing the growth of or killing microorganisms. The OAM is capable of being held or kept in the odor/antimicrobial reduction layer of the present invention.

Preferred OAMs include, but are not limited to, a quaternary ammonium, a phenolic, an amide, an acid, a nitro compounds, and a metalphthalocyanine material, and mixtures thereof. In a preferred embodiment, the OAM is a metalphthalocyanine material.

Preferred quaternary ammonium compounds include 2-(3-anilinovinylul)3,4-dimethyl-oxazolinium iodide, alkylisoquinolium bromide, benzalkonium chloride, benzethonium chloride, cetylpyridium chloride, chlorhexidine gluconate, chlorhexidine hydrochloride, lauryl trimethyl ammonium, methylbenzethonium chloride, stearltrimethylammonium chloride, 2,4,5-trichloro phenoxide, and mixtures thereof.

Preferred phenolic compounds include benzyl alcohol, p-chlorophenol, chloreocresol, chloroxylenol, cresol, o-cymene-5-ol (BIOSOL), hexachlorophene, hinokitiol, isopropylmethylphenol, parabens (having methyl, ethyl, propyl, butyl, isobutyl, isopropyl, and/or sodium methyl substituents), phenethyl alcohol, phenol, phenoxyethanol, o-phynylphenol, resorcin, resorcin monoacetate, sodium parabens, sodium phenolsulfonate, thioxolone, 2,4,4'-trichloro-2'-hydroxydiphenyl ether, zinc phenolsulfonate, and mixtures thereof; more preferably sodium parabens.

Preferred amides include diazolidinyl urea, 2,4-imidazolidinedione (HYDATOIN), 3,4,4'-trichlorocarbanilide, 3-trifluoromethyl-4-4'-dichlorocarbanilide, undecylenic acid monoethanolamide, and mixtures thereof; more preferably diazolidinyl urea and 2,4-imidazolidinedione; more preferably still 2,4-imidazolidinedione.

Preferred acids include benzoate, benzoic acid, citric acide, dehydroacetic acid, potassium sorbate, sodium citrate, sodium dehydroacetate, sodium salicylate, sodium salicylic acid, sorbic acid, undecylenic acid, zinc undecylenate, and mixtures thereof; more preferably benzoic acid, citric acid, salicylic acid and sorbic acid, more preferably still citric acid and sorbic acid.

Preferred nitro compounds include 2-bromo-2-nitro-2,3-propanediol (BRONOPOL), and methyldibromo glutaronitrile and propyulene glycol (MERGUARD), and mixtures thereof.

In a preferred embodiment, the odor/antimicrobial reduction layer includes a metalphthalocyanine material as an odor/antimicrobial material. A preferred metalphthalocyanine material may have the following chemical structure:

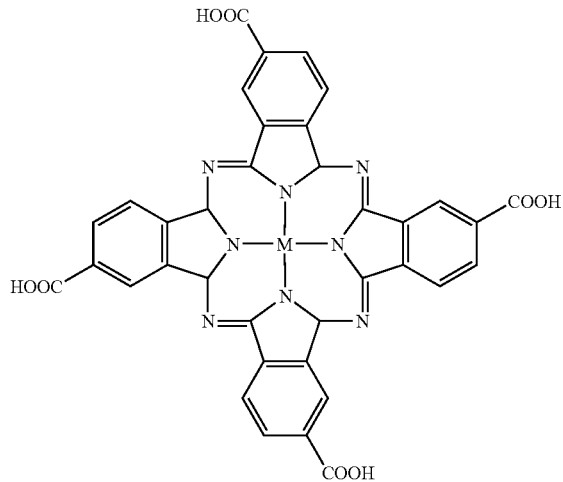

The metalphthalocyanine material has the central metal (indicated by "M" in the above chemical structure) selected from the transition elements. In a preferred embodiment, the central metal of the metalphthalocyanine material is Ni(II), Fe(III), Co(II), or Mn(II). In a more preferred embodiment for use of disposable diapers, the central metal of the metalphthalocyanine material is Fe(III) or Co(II).

Preferred metalphthalocyanine derivatives have —COOH as the functional group. Such preferred metalphthalocyanine derivatives can have either di, tetra or octa forms of —COOH. Alternatively, the metalphthalocyanine derivatives can have either di, tetra or octa forms of —$SO_3Na$.

In a preferred embodiment, the odor/antimicrobial reduction layer includes a carrier means which holds or keeps the metalphthalocyanine material within the fluid storage layer through physical or chemical bonds. Any materials known in the art can be used as the carrier means as long as it can hold or keep the metalphthalocyanine material therein. Preferred carrier means includes fibrous materials such as nonwoven webs, tissue webs, and fluffs of synthetic fibers or natural fibers such as cellulose fibers; foams, apertured polymeric webs or films; and the like. Preferably, at least 95%, more preferably at least 99% by weight of the metalphthalocyanine material is physically bonded to the component material of the carrier means, while the rest of the metalphthalocyanine material may remain unbonded or chemically bonded to some of the component material of the carrier means.

In a preferred embodiment, the carrier means is a nonwoven material. More preferably, the nonwoven material is a resin bonded nonwoven material formed by polyethylene terephthalate (PET) fibers. A preferred resin bonded nonwoven material which can be used as the carrier means is commercially available from PGI Nonwovens, USA, under Code No. 68500.

In an alternative preferred embodiment, the carrier means is formed by a natural fibrous material such as cellulose fibers in the form of fluff, which is conventionally utilized and generally referred to as "airfelt" in absorbent cores (or fluid storage layers).

In a preferred embodiment, the metalphthalocyanine material is dispersed uniformly throughout the carrier means. In an alternative preferred embodiment, the metalphthalocyanine material is dispersed non-uniformly in the carrier means, e.g., the basis weight of the metalphthalocyanine material changes horizontally, vertically or both within the odor/antimicrobial reduction layer. For example, the odor/antimicrobial reduction layer can have a metalphthalocyanine material gradient in the horizontal direction, such as with more metalphthalocyanine material being present in regions of relatively high fluid handling requirements (i.e., near the region of fluid discharge) and less metalphthalocyanine material at lower demand regions. In another example, the basis weight of the metalphthalocyanine material may change in the vertical direction (i.e., the thickness direction) of the odor/antimicrobial reduction layer.

In one embodiment, the metalphthalocyanine material is in the form of discrete particles. In a preferred embodiment, the particles of the metalphthalocyanine material are distributed in a fibrous material of the carrier means to form the odor/antimicrobial reduction layer. Such an odor/antimicrobial reduction layer is typically made by airlaying, wherein an airstream of the particles of the metalphthalocyanine material is metered into an airstream of the fibrous materials of the carrier means. Alternatively, the particles of the metalphthalocyanine material can be laminated between two or more webs of fibrous material such as nonwoven materials to form the odor/antimicrobial reduction layer.

In a preferred embodiment, the basis weight of the odor/antimicrobial reduction layer can range from about 0.002 to 0.012 $g/cm^2$, more preferably from about 0.003 to 0.008 $g/cm^2$, and yet more preferably from about 0.004 to 0.007 $g/cm^2$.

The density and basis weight of the odor/antimicrobial reduction layer does not need to be uniform throughout the layer. The odor/antimicrobial reduction layer can contain regions of relatively higher and relatively lower density and basis weight. The density values for the odor/antimicrobial reduction layer are calculated from basis weight and layer caliper measured under a confining pressure of 0.2 psi (1.43 kPa).

Other materials or agents can be used with the metalphthalocyanine material as an aid in producing the odor/antimicrobial reduction layer. In a preferred embodiment, water is used in conjunction with the metalphthalocyanine material. The water functions to promote uniform dispersion of the metalphthalocyanine material on the surface of the carrier means and permeation of the metalphthalocyanine material into the surface region of the carrier means. The water is used in a proportion of less than about 20 parts by weight (i.e., 0 parts to about 20 parts by weight), preferably in the range of from about 0.01 parts to about 20 parts by weight, more preferably in the range of from about 0.1 parts to about 10 parts by weight, per 100 parts by weight of the carrier means. The actual amount of water to be used will vary depending upon the kind of the component material and the carrier means.

In a more preferred embodiment, a viscosity control agent and/or a binding agent is additionally used in conjunction with the metalphthalocyanine material. The viscosity control agent functions to further promote uniform dispersion of the metalphthalocyanine material on the surface of the carrier means and permeation of the metalphthalocyanine material into the surface region of the carrier means. The binding agent further promotes stronger physical bond between the metalphthalocyanine material and the component material of the carrier means.

In a preferred embodiment wherein the carrier means is a resin bonded nonwoven material formed by polypropylene fibers, a methlose and a carboxy methyl cellulose are used as the viscosity control agent and the binding agent, respectively. The viscosity control agent is used in a proportion of less than about 40 parts by weight (i.e., 0 parts to about 40 parts by weight), preferably in the range of from about 0.01 parts to about 40 parts by weight, more preferably in the range of from about 0.1 parts to about 30 parts by weight, per 100 parts by weight of the carrier means. The binding agent is used in a proportion of less than about 40 parts by weight (i.e., 0 parts to about 40 parts by weight), preferably in the range of from about 0.01 parts to about 30 parts by weight, more preferably in the range of from about 0.1 parts to about 20 parts by weight, per 100 parts by weight of the carrier means. The actual amounts and kinds of the viscosity control agent and the binding agent to be used vary depending upon the kinds of the metalphthalocyanine material and the component material of the nonwoven material.

In a preferred embodiment wherein the carrier means is a resin bonded nonwoven material formed by polyethylene terephthalate (PET) fibers, the metalphthalocyanine material is contained in a mixture with water, a viscosity control agent (e.g., a methlose) and a binding agent (e.g., a carboxy methyl cellulose). The use of the water can provide the preferred penetration of the metalphthalocyanine material into the carrier means while also providing a necessary uniformity of dispersion of the metalphthalocyanine material. However, a mixture of all three agents is more preferred in order to control the amount of the penetration of the metalphthalocyanine material into the carrier means.

The PH of the metalphthalocyanine material solution needs to be controlled (or chosen) depending on the type of the metalphthalocyanine material and the functional group bonded therein. For example, in a preferred embodiment wherein the metalphthalocyanine material has a tetra –COOH as the functional group, the PH of the metalphthalocyanine material solution is controlled between about 3 and 6, more preferably between about 4 and 5.

The metalphthalocyanine material solution may be applied to the carrier means by any of various techniques and apparatus used for applying solutions to materials including coating, dumping, pouring, spraying, atomizing, or immersing the solution on the carrier means. In a preferred embodiment, the metalphthalocyanine material solution is applied onto at least a portion of the carrier means. Preferably, the metalphthalocyanine material solution is coated onto the entire surface of most, preferably all, of the carrier means.

Alternatively, the metalphthalocyanine material solution can be generally mixed with component fibers of the carrier means before the formation of the carrier means. The method of mixing can be done by any of a number of mixing techniques and mixing apparatus known in the art as long as the component fibers of the carrier means can be fully coated with the metalphthalocyanine material solution. After the component fibers are thoroughly coated with the metalphthalocyanine material solution, the formation for the carrier means is carried out to form the odor/antimicrobial reduction layer.

The fluid storage layer can include a single layer of essentially 100% superabsorbent material. Alternatively, the fluid storage layer can include a single layer of essentially 100% non-superabsorbent material such as the material(s) described below as a carrier means. Preferably, the fluid storage layer includes a superabsorbent material and a carrier means for the superabsorbent material. The carrier means may be manufactured from a wide variety of liquid-absorbent materials commonly used in disposable diapers and other absorbent articles such as comminuted wood pulp which is generally referred to as airfelt. Examples of other carrier means include creped cellulose wadding; meltblown polymers including coform; chemically stiffened, modified or cross-linked cellulosic fibers; tissue including tissue wraps and tissue laminates; absorbent foams; absorbent sponges; or any equivalent material or combinations of materials.

The fluid storage layer preferably includes at least 15%, by weight, preferably at least 25%, of superabsorbent material (defined more fully hereafter), and from 0% to about 85%, preferably less than about 75%, of the carrier means. However, the fluid storage layer may include about 0% by weight of superabsorbent material and about 100% of the carrier means. The principal function of the fluid storage layer is to absorb discharged body fluid and retain such fluid under the pressures encountered as a result of the wearer's movements.

As indicated hereinbefore, the fluid storage layer preferably includes superabsorbent material such as, but not necessarily limited to, discrete particles of absorbent gelling material and superabsorbent fibrous material such as acrylate grafted fibers and superabsorbent modified cellulosic fibers. The superabsorbent material can be in any form which can be incorporated into the fibrous material of the carrier means to form the fluid storage layer. Superabsorbent materials are described in more detail below. The superabsorbent material, upon contact with fluids such as water or body fluids, absorb such fluids. The fluid discharged into the disposable absorbent article and transported to the fluid storage layer can be acquired and held by the superabsorbent material, thereby providing the articles herein with enhanced absorbent capacity and/or improved fluid retention performance.

The superabsorbent materials are those which are capable of absorbing at least about 10 g, preferably at least about 15 g, more preferably at least about 20 g, of Synthetic Urine (1.0% NaCl aqueous solution) per gram of superabsorbent material, as determined according to the hereinafter described Absorbent Capacity procedure.

The superabsorbent material utilized herein is typically in the form of discrete particles of absorbent gelling material. These particles are preferably distributed within a fibrous material of the carrier means. The fluid storage layer which has particles of the absorbent gelling material distributed in fibrous materials of the carrier means is typically made by airlaying, wherein an airstream of the particles of the absorbent gelling material is metered into an airstream of the fibrous materials of the carrier means. The superabsorbent fibrous material can include synthetic or natural fibers. Suitable natural fibrous material for the carrier means are cellulose fibers, in the form of fluff, such as is conventionally utilized and generally referred to as "airfelt" in absorbent cores (or fluid storage layers).

The average dry density of the fluid storage layer including the carrier means is generally in the range of from about 0.06 to about 0.5 g/cm$^3$, more preferably within the range of from about 0.10 to about 0.4 g/cm$^3$, yet more preferably from about 0.15 to about 0.3 g/cm$^3$, and still more preferably from about 0.15 to about 0.25 g/cm$^3$. Typically the basis weight of the fluid storage layer can range from about 0.02 to 0.12 g/cm$^2$, more preferably from about 0.04 to 0.08 g/cm$^2$, and yet more preferably from about 0.05 to 0.07 g/cm$^2$.

The density and basis weight of the fluid storage layer does not need to be uniform throughout the layer. The fluid storage layer can contain regions of relatively higher and relatively lower density and basis weight. The density values for the fluid storage layer are calculated from basis weight and layer caliper measured under a confining pressure of 0.2 psi (1.43 kPa). The density and basis weight values include the weight of the superabsorbent material. Additionally, the fluid storage layer can have a superabsorbent material gradient, such as with more superabsorbent material being present in regions of relatively high fluid handling requirements (i.e., near the region of fluid discharge) and less superabsorbent material at lower demand regions.

Preferably, the superabsorbent material which is employed in the fluid storage layer is a substantially water-insoluble, slightly cross-linked, partially neutralized, polymeric absorbent gelling material. This material forms a hydrogel upon contact with water. Such polymer materials can be prepared from polymerizable, unsaturated, acid-containing monomers. Suitable unsaturated acidic monomers for use in preparing the polymeric gelling material include those disclosed in U.S. Pat. No. 4,654,039 issued to Brandt et al. on Mar. 31, 1987 and reissued as U.S. Pat. No. Re. 32,649 on Apr. 19, 1988. Preferred monomers include acrylic acid, methacrylic acid, and 2-acrylamido-2-methyl propane sulfonic acid. Acrylic acid is especially preferred for preparation of the polymeric gelling agent material.

The polymeric component formed from unsaturated, acid-containing monomers may be grafted on to other types of polymer moieties such as starch or cellulose. Polyacrylate grafted starch materials of this type are also especially preferred.

Preferred polymeric absorbent gelling materials which can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric absorbent gelling material particles, such materials will in general be slightly cross-linked. Cross-linking agents serves to render the hydrogel-forming polymer gelling materials substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in U.S. Pat. No. 4,076,663 issued to Masuda et al. on Feb. 28, 1978. Preferred cross-linking agents are the di- or polyesters of unsaturated mono- or polycarboxylic acids with polyols, the bisacrylamides and the di- or triallyl amines. Other preferred cross-linking agents are N,N'-methylenebisacrylamide, trimethylol propane triacrylate and triallyl amine. The cross-linking agent can generally constitute from about 0.001 mole percent to 5 mole percent of the resulting hydrogel-forming polymer material. More preferably, the cross-linking agent will constitute from about 0.01 mole percent to 3 mole percent of the hydrogel-forming polymeric gelling material particles used herein.

The slightly cross-linked, hydrogel-forming polymeric gelling material particles are generally employed in their partially neutralized form. Such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

Alternatively, the particles of absorbent gelling material can be laminated between two or more webs of fibrous material to form the fluid storage layer, such as exemplified in U.S. Pat. No. 4,578,068 issued to Kramer et al. on Mar. 25, 1986.

The isolation means can be formed by any structure which can work for the isolation of the metalphthalocyanine material from the superabsorbent material. Such a structure for the isolation can be any structure which spaces the metalphthalocyanine material in the odor/antimicrobial reduction layer away from contacting the superabsorbent material. In a preferred embodiment, the isolation means is an interposed material disposed between the fluid storage layer and the odor/antimicrobial reduction layer. Preferred interposed materials for the isolation means include fibrous materials such as nonwoven webs, tissue webs, and fluffs of synthetic fibers or natural fibers such as cellulose fibers; foams, apertured polymeric webs or films; and the like. In a preferred embodiment, the isolation means is a tissue layer or a non-woven layer which is disposed between the fluid storage layer and the odor/antimicrobial reduction layer. In a more preferred embodiment, such a tissue or nonwoven layer is also used for enveloping at least a part of, more preferably the entire portion of the fluid storage layer.

The basis weight of the isolation means can range from about 0.001 to 0.008 g/cm$^2$, more preferably from about 0.0012 to 0.006 g/cm$^2$, and yet more preferably from about 0.0013 to 0.005 g/cm$^2$. In a preferred embodiment wherein the interposed material is a nonwoven material, the basis weight of the tissue material is about 0.0049 g/cm$^2$.

The density and basis weight of the interposed material does not need to be uniform throughout the material. The interposed material can contain regions of relatively higher and relatively lower density and basis weight. The density values for the interposed material are calculated from basis weight and material caliper measured under a confining pressure of 0.2 psi (1.43 kPa). A preferred tissue material to be used as the interposed material is available from Fripa Co., Ltd., under Code No. 1110000.

Particularly preferred embodiments of the disposable absorbent article are disclosed hereinafter by referring to the drawing. Herein, "absorbent article" refers to devices which absorb and contain body exudates, and, more specifically, refers to devices which are placed against or in proximity to the body of the wearer to absorb and contain the various exudates discharged from the body. Herein, "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A preferred embodiment of the disposable absorbent article of the present invention is a unitary disposable diaper 20, shown in FIGURE. Herein, "unitary" absorbent article refers to absorbent articles which are formed of separate parts united together to form a coordinated entity so that they do not require separate manipulative parts like a separate holder and liner. Herein, "diaper" refers to an absorbent article generally worn by infants and incontinent persons that is worn about the lower torso of the wearer. It should be understood, however, that the present invention is also applicable to other disposable absorbent articles such as disposable underwears, disposable diapers (adult and baby) including pull-on diapers and training pants, disposable panties for menstrual use, and disposable absorbent pads including sanitary napkins.

FIGURE is a plan view of the disposable diaper 20 in its flat-out, uncontracted state (i.e., with elastic induced contraction pulled out) with portions of the structure being cut-away to more clearly show the construction of the diaper 20 and with the portion of the diaper 20 which faces the wearer, the body-facing surface 40, facing the viewer. As shown in FIGURE, the diaper 20 preferably comprises a chassis 22 comprising a liquid pervious topsheet 24; a liquid impervious backsheet 26 joined to the topsheet; and a fluid storage layer 28 positioned between the topsheet 24 and the backsheet 26. The fluid storage layer 28 has a pair of opposing longitudinal edges 60. The diaper preferably further comprises side panels 30; elasticized leg cuffs 32; elasticized waistbands 34; and a fastening system 36 preferably comprising a pair of securement members 37 and a landing member 38.

The diaper 20 is shown in FIGURE to have a body-facing surface 40 (facing the viewer in FIGURE), a garment-facing surface 42 opposed to the body-facing surface 40, a back region 44, a front region 46 opposed to the back region 44, a crotch region 48 positioned between the back region 44 and the front region 46, and a periphery which is defined by the outer perimeter or edges of the diaper 20 in which the side edges are designated 50 and the end edges are designated 52. The body-facing surface 40 of the diaper 20 comprises that portion of the diaper 20 which is positioned adjacent to the wearer's body during use (i.e., the body-facing surface 40 generally is formed by at least a portion of the topsheet 24 and other components joined to the topsheet 24). The garment-facing surface 42 comprises that portion of the diaper 20 which is positioned away from the wearer's body (i.e., the garment-facing surface 42 is generally formed by at least a portion of the backsheet 26 and other components joined to the backsheet 26). The back region 44 and the front region 46 extend from the end edges 52 of the periphery to the crotch region 48.

The diaper 20 also has two centerlines, a longitudinal centerline 100 and a transverse centerline 110. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The chassis 22 comprises the topsheet 24, the backsheet 26 and the fluid storage layer 28 having the pair of opposing longitudinal edges 60, the body-facing surface, and the garment-facing surface. The body-facing surface generally faces the body of the wearer while the garment-facing surface generally faces away from the body of the wearer (and the garment of the wearer). When the absorbent article comprises a separate holder and a liner, the chassis 22 generally comprises the holder and the liner (i.e., the chassis 22 comprises one or more layers of material to define the holder while the liner comprises an absorbent composite such as a topsheet, a backsheet, and a fluid storage layer.) For unitary absorbent articles, the chassis 22 preferably comprises the topsheet 24, the backsheet 26 and the fluid storage layer 28 of the diaper with other features added to form the composite diaper structure.

In the embodiment shown in FIGURE, the topsheet 24 and the backsheet 26 have length and width dimensions generally larger than those of the fluid storage layer 28. The topsheet 24 and the backsheet 26 extend beyond the edges of the fluid storage layer 28 to thereby form the periphery of the diaper 20. While the topsheet 24, the backsheet 26, and the fluid storage layer 28 may be assembled in a variety of well known configurations, exemplary chassis configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

The fluid storage layer 28 may be any absorbent member which is generally compressible, conformable, non-irritating to the wearer's skin, and capable of absorbing and retaining liquids such as urine and other certain body exudates. As shown in FIGURE, the fluid storage layer 28 has a garment-facing side, a body-facing side, a pair of side edges, and a pair of waist edges. The fluid storage layer 28 may be manufactured in a wide variety of sizes and shapes (e.g., rectangular, hourglass, "T"-shaped, asymmetric, etc.). Preferably, the fluid storage layer 28 includes a superabsorbent material and a carrier means for the superabsorbent material. In this embodiment, the carrier means is preferably formed from comminuted wood pulp which is generally referred to as airfelt.

The configuration and construction of the fluid storage layer 28 may vary (e.g., the fluid storage layer may have varying caliper zones, a hydrophilic gradient, a superabsorbent gradient, or lower average density and lower average basis weight acquisition zones; or may comprise one or more layers or structures). Further, the size and absorbent capacity of the fluid storage layer 28 may also be varied to accommodate wearers ranging from infants through adults. However, the total absorbent capacity of the fluid storage layer 28 should be compatible with the design loading and the intended use of the diaper 20.

One embodiment of the diaper 20 has an asymmetric, modified T-shaped fluid storage layer 28 having ears in the front region but a generally rectangular shape in the back region. Exemplary absorbent structures for use as the fluid storage layer 28 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The fluid storage layer may further comprise the dual core system containing an acquisition/distribution core of chemically stiffened fibers positioned over a fluid storage layer as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992.

In a preferred embodiment, the diaper 20 further includes an odor/antimicrobial reduction layer (not shown in FIGURE) of the present invention which is disposed between the topsheet 24 and the fluid storage layer 28. Alternatively, the odor/antimicrobial reduction layer may be disposed between the backsheet 26 and the fluid storage layer 28.

In these embodiments, an isolation means (not shown in FIGURE) is formed by a tissue or nonwoven material which envelops at least a part of, preferably the entire portion of the material of the carrier means. The portion of the isolation layer which disposed between the fluid storage layer and the odor/antimicrobial reduction layer isolates the metalphthalocyanine material from contacting the superabsorbent material contained in the fluid storage layer 28. Preferably, the odor/antimicrobial reduction layer is disposed on the either the body-facing surface or the garment-facing surface of the fluid storage layer 28 such that it can be in contact with of the fluid storage layer.

In an alternative preferred embodiment, the isolation means (not shown in FIGURE) is formed by a separate material from such a fluid storage layer enveloping material (i.e., a tissue or nonwoven material). Preferably, such a separate material (i.e., an isolation means) is disposed between the odor/antimicrobial reduction layer and the fluid storage layer 28. A preferred separate material is a nonwoven material.

The topsheet 24 is preferably positioned adjacent the body-facing surface of the fluid storage layer 28 and is preferably joined thereto and to the backsheet 26 by attachment means (not shown) such as those well known in the art. Suitable attachment means are described with respect to joining the backsheet 26 to the fluid storage layer 28. In a preferred embodiment, the topsheet 24 and the backsheet 26 are joined directly to each other in the diaper periphery and are indirectly joined together by directly joining them to the fluid storage layer 28 by any suitable attachment means.

The topsheet 24 is preferably compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred nonwoven material for the topsheet 24 is a carded nonwoven material of polypropylene which available from Amoco Fabrics, under Code No. Soft P-10, 23 Stly 007.

The topsheet 24 is preferably made of a hydrophobic material to isolate the wearer's skin from liquids which have passed through the topsheet 24 and are contained in the fluid storage layer 28 (i.e. to prevent rewet). If the topsheet 24 is made of a hydrophobic material, at least the body-facing surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the fluid storage layer 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991.

An alternative preferred topsheet 24 comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991.

The backsheet 26 is that portion of the diaper 20 which is generally positioned away from the wearer's skin and which prevents the exudates absorbed and contained in the fluid storage layer 28 from wetting articles which contact the diaper 20 such as bedsheets and undergarments. Thus, the backsheet 26 is preferably impervious to liquids (e.g., urine) and is preferably manufactured from a thin plastic film, although other flexible liquid impervious materials may also be used. (As used herein, the term "flexible" refers to materials which are compliant and will readily conform to the general shape and contours of the human body.) However, the backsheet 26 permits vapors to escape from the diaper 20. A suitable material for the backsheet 26 is a thermoplastic film having a thickness of from about 0.012 mm (0.5 mil) to about 0.051 mm (2.0 mils), preferably comprising polyethylene or polypropylene.

The backsheet 26 is preferably positioned adjacent the garment-facing surface of the fluid storage layer 28 and is preferably joined thereto by any suitable attachment means known in the art. For example, the backsheet 26 may be secured to the fluid storage layer 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat.

No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

Embodiments are also contemplated wherein the fluid storage layer 28 is not joined to the backsheet 26, and/or the topsheet 24 in order to provide greater extensibility in the front region 46 and the back region 44. Alternative embodiments are contemplated wherein an additional member, such as a liquid impervious barrier material(s) (not shown), is positioned between the garment-facing surface of the fluid storage layer 28 and the backsheet 28. Any such barrier member may or may not be joined to the fluid storage layer 28. Further, the backsheet 26 may or may not be joined to any barrier material(s) that are positioned between the backsheet 26 and the fluid storage layer 28.

The diaper 20 preferably further comprises an outer cover (not shown in FIGURE) joined with at least a portion of the garment-facing surface of the backsheet 26 forming a laminate. The outer cover preferably comprises a nonwoven material. (However, embodiments are contemplated wherein the outer cover comprises materials such as woven webs, foams, scrims, films, loose fibers, or any other material or combination of materials known in the art that will give the diaper a cloth-like look and/or feel and is at a minimum air permeable.) The outer cover may cover all or substantially all of the garment-facing surface of the backsheet 26, or may cover only discrete predetermined portions. In a preferred embodiment, the nonwoven material of the outer cover covers all or substantially all of the backsheet 26 in order to provide the diaper with a cloth-like look and feel. Further, the outer cover may provide the diaper with a low cost landing zone capable of engaging the hooks of a hook and loop type fastener. (Such a landing zone could be utilized as a portion of a primary fastening system or as a means for disposing of a soiled diaper.) Alternatively, the outer cover may cover only specific portions of the backsheet 26, such as the garment-facing surface of the side panels 30. In one such embodiment, the outer cover is comprised in the breathable side panels 30. Thus, the outer cover may provide extra strength, bulk, aesthetic appeal or other characteristics desired in the breathable side panels 30.

The nonwoven material comprised in the outer cover is preferably liquid and air pervious. The nonwoven material may comprise natural fibers (e.g. cotton or wood fibers), or may comprise fibers of polyethylene, polypropylene, polyester, or any combination of such fibers. Further, the nonwoven may be carded, spunmelt, meltblown or air-through bonded or have any other characteristic or be manufactured in any manner known in the art. Preferably, the nonwoven is comprised of sufficient thermoplastic material to allow for thermal bonding of the material to other components of the diaper.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment.

It is preferred that each elasticized leg cuff 32 comprise at least an inner barrier cuff 70 comprising a barrier flap 68 and a spacing element 69 such as described in the above-referenced U.S. Pat. No. 4,909,803. In a preferred embodiment, the elasticized leg cuff 32 additionally comprises an elastic gasketing cuff 63 with one or more elastic strands 65, positioned outboard of the barrier cuff such as described in the above-referred U.S. Pat. No. 4,695,278. Further, the elasticized leg cuff 32 preferably has a proximal edge 33 and a distal edge 35. The distal edge 35 of the elasticized leg cuff 32 is that part of the elasticized leg cuff 32 which is spaced away from the chassis 22 of the diaper when the diaper 20 is being worn. The proximal edge 33 is that part of the elasticized leg cuff 32 which is joined to the chassis 22 of the diaper 20. The proximal edge 33 is generally located laterally inboard of the periphery of the diaper 20.

It may also be desirable to provide the diaper 20 with extensibility or elasticity in all or a portion of the side panels 30. (Herein, "extensible" refers to materials that are capable of extending in at least one direction to a certain degree without undue rupture. Herein, "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 30 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 30 further provide more effective application of the diaper 20 since even if the diaperer pulls one side panel 30 farther than the other during the application (asymmetrically), the diaper 20 will "self-adjust" during wear. While the extensible side panels 30 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and in U.S. Pat. No. 5,151,092 issued to Buell et al. on Sep. 29, 1992.

The diaper 20 preferably further comprises an elasticized waistband 34 that provides improved fit and containment. The elasticized waistband 34 is that portion or zone of the diaper 20 which is intended to elastically expand and contract to dynamically fit the wearer's waist. The elasticized waistband 34 preferably extends longitudinally outwardly from at least one of the waist edges of the fluid storage layer 28 and generally forms at least a portion of the end edge of the diaper 20. Disposable diapers are generally constructed so as to have two elasticized waistbands, one positioned in the back region and one positioned in the front region, although diapers can be constructed with a single elasticized waistband. Further, while the elasticized waistband 34 or any of its constituent elements can comprise a separate element affixed to the diaper 20, the elasticized waistband 34 may be constructed as an extension of other elements of the diaper such as the backsheet 26 or the topsheet 24, preferably both the backsheet 26 and the topsheet 24. The elasticized waistband 34 may be constructed in a number of different configurations including those described in U.S. Pat. No. 4,515,595 entitled "Disposable Diapers With Elastically Contractible Waistbands" issued to Kievit & Osterhage on May 7, 1985, and in U.S. Pat. No. 5,151,092 entitled "Absorbent Article With Dynamic Elastic Waist Feature Having A Predisposed Resilient Flexural Hinge" issued to Buell, Clear & Falcone on Sep. 29, 1992; and elasticized waistbands made from a structural elastic-like film (SELF) web as described in the previously referenced WO 95/03765.

In a preferred embodiment, the elasticized waistband 34 includes a laminate of a first nonwoven coverstock layer, an elastomeric layer, and more preferably a second nonwoven coverstock layer. The elastomeric layer can be formed by any elastomeric materials known in the art. The elasticized waistband 34 is preferably disposed on the body-facing surface or the garment-facing surface of the topsheet 24 and operatively joined in an elastically contractible condition with the topsheet 24 to gather the elasticized waistband 34.

The diaper 20 also comprises a fastening system 36 which forms a side closure which maintains the back region 44 and the front region 46 in an overlapping configuration such that lateral tensions are maintained around the circumference of the diaper to maintain the diaper on the wearer. Exemplary fastening systems are disclosed in U.S. Pat. No. 3,848,594 issued to Buell on Nov. 19, 1974; U.S. Pat. No. 4,662,875 issued to Hirotsu and Robertson on May 5, 1987; U.S. Pat. No. 4,869,724 issued to Scripps on Sep. 26, 1989; U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; and U.S. Pat. No. 5,326,612 entitled "Nonwoven Female Component For Refastenable Fastening Device And Method of Making the Same" issued to David J. K. Goulait on Jul. 5, 1994.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
    a topsheet,
    a backsheet joined to the topsheet,
    a fluid storage layer disposed between the topsheet and the backsheet and having a body-facing surface and a garment-facing surface opposing the body-facing surface, wherein said topsheet is positioned adjacent to said body-facing surface of said fluid storage layer; and
    an odor/antimicrobial reduction layer disposed on said body facing surface of said fluid storage layer, the odor/antimicrobial reduction layer containing an odor/antimicrobial reduction material.

2. The disposable article of claim 1, wherein the odor/antimicrobial reduction layer has a predetermined pattern of the odor/antimicrobial reduction material.

3. The disposable article of claim 2, wherein the predetermined pattern includes a more-treated region by the odor/antimicrobial material, and a less-treated region of the odor/antimicrobial material.

4. The disposable absorbent article of claim 2, wherein the predetermined pattern includes droplets, discrete dots, stripes, shapes, printed pictures and characters.

5. The disposable absorbent article of claim 3, wherein the predetermined pattern includes a plurality of stripes each having a width from about 0.1 cm to about 10 cm, and wherein the stripes are spaced apart by the less-treated region(s) by the odor/antimicrobial material each having a width from about 0.12 cm to about 10 cm.

6. The disposable absorbent article of claim 1, wherein the odor/antimicrobial material is selected from the group consisting of quaternary ammonium, a phenolic, an amide, an acid, a nitro compound, a metalphthalocyanine material, and mixtures thereof.

7. The disposable absorbent article of claim 1, wherein the odor/antimicrobial material is a metalphthalocyanine material which has the central metal selected from the transition elements.

8. The disposable absorbent article of claim 7, wherein the central metal is Ni(II), Fe(III), Co (II), or Mn (II).

9. The disposable absorbent article of claim 1, wherein the odor/antimicrobial reduction layer is disposed adjacent to the body-facing surface of the fluid storage layer.

10. The disposable absorbent article of claim 1, wherein the odor/antimicrobial reduction layer further includes a carrier means, and wherein the odor/antimicrobial material is applied to the carrier means.

11. The disposable absorbent article of claim 10, wherein the odor/antimicrobial material includes at least about from 0.001% to about 10%, by weight, a metalphthalocyanine material, and from about 90% to about 99.999% of a carrier means.

* * * * *

UNITED STATES PATENT AND TRADEMARK OFFICE
CERTIFICATE OF CORRECTION

PATENT NO. : 7,655,828 B2 Page 1 of 1
APPLICATION NO. : 11/114490
DATED : February 2, 2010
INVENTOR(S) : Rajagopalan It is certified that error appears in the above-identified patent and that said Letters Patent is hereby corrected as shown below:

Column 2
Line 5, delete "No. 145-277143" and insert --No. H5-277143--.

Column 20
Line 31, delete "0.12" and insert --0.1--.

Signed and Sealed this

Twenty-seventh Day of July, 2010

David J. Kappos
*Director of the United States Patent and Trademark Office*